United States Patent [19]
Thomas et al.

[11] Patent Number: 5,564,279
[45] Date of Patent: Oct. 15, 1996

[54] FREEZING BAGS

[75] Inventors: Michael J. G. Thomas, Farnham; Susan H. Bell, Southampton, both of Great Britain; Joseph Goertz, Nes A/D Amstel; Hubertus E. Hilbrink, Emmen, both of Netherlands

[73] Assignee: The Secretary of State for Defence in Her Britannic Majesty's Government of the United Kingdom of Great Britain and Northern Ireland, Whitehall, England

[21] Appl. No.: 392,858

[22] PCT Filed: Aug. 27, 1993

[86] PCT No.: PCT/GB93/01829

§ 371 Date: Mar. 17, 1995

§ 102(e) Date: Mar. 17, 1995

[87] PCT Pub. No.: WO94/05247

PCT Pub. Date: Mar. 17, 1994

[30] Foreign Application Priority Data

Sep. 2, 1992 [GB] United Kingdom .................. 9218538

[51] Int. Cl.$^6$ .................................... B65B 63/08
[52] U.S. Cl. ............................... 62/60; 62/64
[58] Field of Search ............................... 62/60, 64

[56] References Cited

U.S. PATENT DOCUMENTS

| 4,194,369 | 3/1980 | Faust et al. | 62/60 |
| 4,251,995 | 2/1981 | Pert et al. | 62/60 |
| 4,470,264 | 9/1984 | Morris | 62/60 |
| 4,565,073 | 1/1986 | Lavender | 62/341 |
| 4,630,448 | 12/1986 | Bilstad et al. | 62/60 |

Primary Examiner—Ronald C. Capossela
Attorney, Agent, or Firm—Nixon & Vanderhye

[57] ABSTRACT

A freezing bag (10) for the storage of blood cells is formed from two sheets (11) of material joined together with welds (15, 18) defining a containment zone (19). A pocket (20) leads from the containment area (19) and in the weld (18) defining this pocket is an access port (17). An access tube (23) is secured to the port (17) and normally lies within the bounds of a pouch (21) formed by extensions of the sheets (11) beyond the containment zone (19).

21 Claims, 4 Drawing Sheets

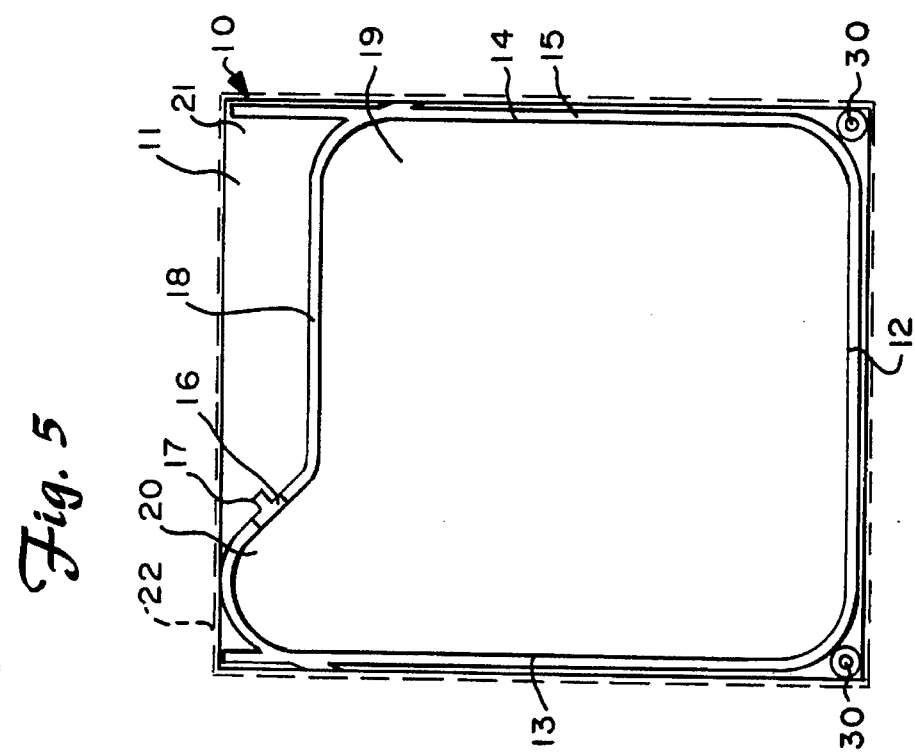
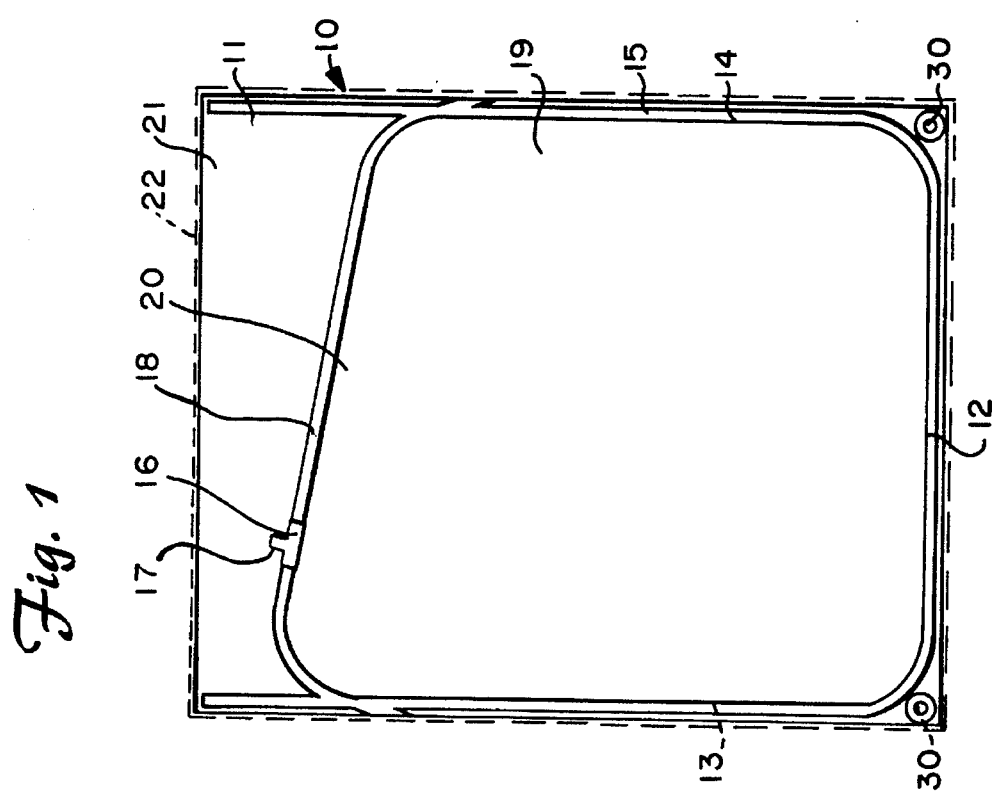

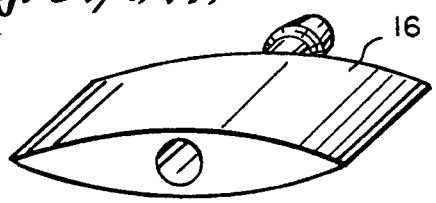
Fig. 3(A)(1)
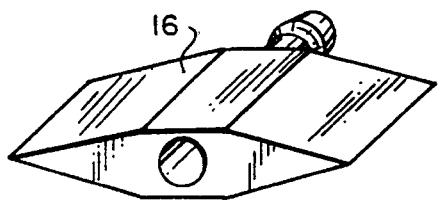
Fig. 3(B)
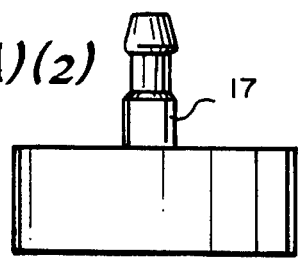
Fig. 3(A)(2)
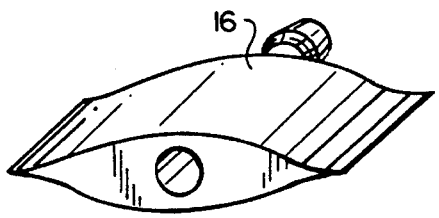
Fig. 3(C)
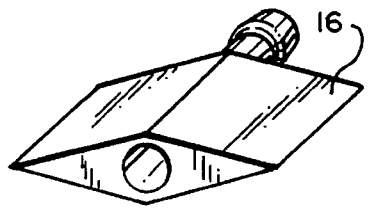
Fig. 3(D)

FREEZING BAGS

BACKGROUND OF THE INVENTION

1. Field of the Invention

The present invention relates to bags for use in the preservation of blood cells.

2. Discussion of Prior Art

Blood used for transfusion is normally stored in refrigerators, at a temperature of 4°±2°, where its safe life is no longer than six weeks. Potentially longer storage life might be obtained by freezing, but unfortunately freezing blood as obtained from a donor results in destruction of the red blood cells making the blood totally unsuitable for transfusion. Red blood cells can be stored after separation from other blood components, by centrifuging, plasma, mixing with a cryoprotectant, and then freezing. The usual cryoprotectant is glycerol. As glycerol itself is poisonous frozen cells must have all the glycerol removed therefrom before being used for transfusion. The necessary removal process, involving centrifugation and multiple washing steps, is a skilled and time-consuming task which also results in a significant loss of viable blood cells.

Another cryoprotectant is hydroxyethyl starch (HES), which is a widely used artificial plasma expander and is non-toxic. Much work has been carried out on methods of preserving red blood cells using this substance. Early efforts were unsuccessful, as it was found that the level of haemolysis (breakdown of red blood cells) in units of blood (a unit of blood being the volume of a standard donation, about 450 ml) recovered after freezing was above the safe limit. It is usually considered that a unit of blood is safe for transfusion if the level of haemolysis at thaw is no greater than 1%. A method of preserving and recovering red blood corpuscules by freezing, using HES as a cryoprotectant, wherein the level of haemolysis after recovery is within acceptable limits, has now been developed and is described in Patent Application PCT/GB90/0140.

The bags used in the method of PCT/GB90/0140 must be capable of fulfilling stringent criteria. Freezing is carried out in liquid nitrogen, and is accompanied by unavoidable changes in volume of the mixture of red blood cells and cryoprotectant. As explained in PCT/GB90/0140 the manner in which this change of volume is accommodated by control of the thickness of the freezing bag during freezing is critical. It is also important that the concentration of HES is within stringent limits, and that the process of transferring donated blood to the freezing bag is carried out in a sterile manner.

It has been suggested that the HES be stored in the freezing bag itself. However it has been found that the materials suitable for manufacturing the bag are slightly porous, allowing the concentration of HES therein to vary, the nature of the variation being dependant on the atmospheric humidity of the storage area.

It is also important that the bags, which must, once filled with blood, be stored at sub-zero temperatures of, for example −100°, should be of a convenient shape for storage. It must also be possible to allow the blood, after thawing to flow from the bag in a sterile manner for transfusion purposes. Bags which fulfil these criteria are described in Patent Applications WO 89/04280 and WO 91/11968. The manner of extraction from these involves penetration by a needle of a special port built into the bag. This procedure requires skill, presents the blood in a format not usually recognised by nursing staff, and also breaches the absolute microbiological integrity of the bag. A fluid storage bag having a single port, described as an outlet port, is illustrated in U.S. Pat. No. 4,256,333. The port is formed from a tube attached to the bag and a closure, and the disclosure is concerned with details of the joint between the tube and the closure.

SUMMARY OF THE INVENTION

According to the present invention, a freezing bag includes two sheets of material joined together by a weld to define a containment zone having a bottom edge, two side edges and an access edge, characterised in that there is a single access port in the access edge and in that the sheets of material extend beyond the limits of the containment zone to form an open pouch, the pouch being defined by the access edge of the containment zone, extensions of the weld forming the side edges of the containment zone, and ends of the sheets.

The port is preferably situated in a pocket defined in part by at least part of the access edge and which leads into the containment zone.

A tube is positioned on the port, and may be secured thereto, by, for example, a small metal collar. The tube may be pre-formed to lie within the bounds of the pouch.

The port is preferably formed integrally with an insert which is positioned in the access edge of the bag prior to welding of that edge.

The pocket in the access edge of the bag may be formed by angling of that edge at other than a right angle to the side edges.

A fluid storage container having pouches is described in U.S. Pat. No. 3,520,471, in which two fluid collecting conduits are positioned in a pouch at one end of the container and a fluid dispensing conduit is positioned in a pouch at an opposite end of the container.

According to another aspect of the present invention a method of freezing red blood cells includes;

- taking a freezing bag, the bag being formed from two sheets of material welded together to form a containment zone having a bottom edge, two side edges and an access edge, at least part of the access edge defining part of a pocket which leads into the containment zone, that part of the access edge having therein an insert having a port to which is attached a tube, the tube lying within an open pouch formed by extensions of the sheets beyond the extent of the bag;
- sterile docking the tube to a supply of centrifuged red blood cells and transferring the red blood cells to the bag;
- disconnecting the supply of red blood cells, sterile docking the tube to a supply of HES, and transferring the HES to the bag;
- manipulating the bag to expel, as far as is practical, all air therefrom;
- sealing the tube and then breaking the docking to the HES supply;
- agitating the contents of the bag to thoroughly mix the blood cells and the HES; and
- placing the bag in a freezing frame and freezing the contents by immersing the frame and bag in liquid nitrogen.

The tube adjacent the port may be clipped during the freezing process.

Before immersing the bag in liquid nitrogen the pouch may be treated. For example by rollers or in a press, to expel air therefrom, and its open end sealed, the arrangement being such that the tube is completely contained within the sealed pouch.

The relative proportions of red blood cells, freezing methods, and methods of recovery of the frozen cells in a form suitable for transfusion, along with other details of the process, are fully described elsewhere, for example in WO 90/09184, and will not be further described here.

Once the blood has been prepared for transfusion the sealed pouch can be breached and the tube connected to standard transfusion apparatus in the conventional manner.

In order to fulfil the requirements of PCT/GB90/140 the containment zone preferably has an area of approximately 0.102 square meters, and the weld, at least at the corners between the side edges and the bottom edges, is radiussed.

BRIEF DESCRIPTION OF THE DRAWINGS

Some embodiments of the invention will now be described, by way of example only, with reference to the accompanying diagrammatic drawings, of which:

FIG. 1 is a plan view of a freezing bag according to the invention.

FIGS. $3A_1$, $3A_2$, B, C and D are a perspective views of four alternative versions of insert as shown in FIG. 2, FIGS. 5 and 6 and 7 are plan views of alternative designs of the bag shown in FIG. 1.

DETAILED DESCRIPTION OF PREFERRED EMBODIMENTS

Figure 2:
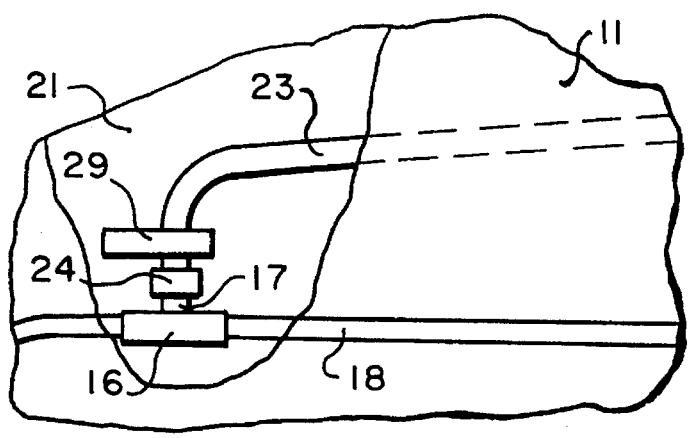
FIG. 2 is a detail of part of the freezing bag shown in FIG. 1.

A freezing bag 10 (FIG. 1) is formed from two sheets of material, shown generally at 11. A bottom edge 12 and side edges 13, 14 of the sheets are joined together by a first weld 15. An insert 16 having an integral port 17 is positioned towards the top of and between the sheets 11 and the sheets 11 are joined together by a second weld 18 which is angled upwardly (relative to a right angle) from the weld 15 at one side 14 of the sheets 11, and which defines an access edge, overlies the insert 16 such that there is a passage across the weld 18, then curves downwardly to meet the weld 15 at the side 14 of the sheets 11. The welds 15, 18 thus define a containment zone 19 which is sealed other than through the insert 16 and port 17, and the insert 16 is positioned towards the top of a pocket 20 defined by the normal to the weld 15 at its junction with the weld 18 and the weld 18.

An open pouch 21 is defined by the extent of the sheets 11 beyond the containment zone 19 and pocket 20, the pouch being defined by the weld 18, extensions of the weld 15, and ends 22 of the sheets 11. A tube 23 (not shown in FIG. 1, but see FIG. 2) is attached to the port 17 and is secured thereto by a metal collar 24.

Suitable shapes of insert 16 are illustrated in FIG. 3.

Figure 4:
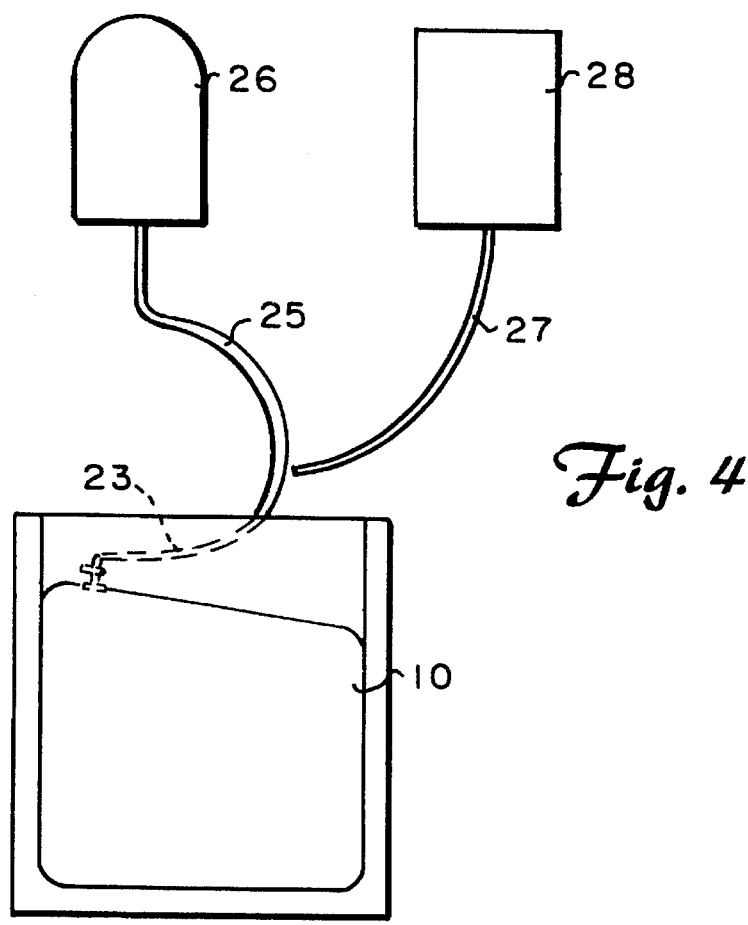
FIG. 4 is a plan view of the bag in use.

In use (FIG. 4) the bag 10 is removed from store and the tube 23 is sterilely docked to a supply tube 25 which leads from a blood bag 26 containing red blood cells (which may be buffy coat depleted), obtained from a standard unit blood donation by means, such as centrifuging, etc., well known in the art, and the blood cells are transferred to the containment zone 19. The supply tube 25 is then disconnected and a tube 27, leading from a HES supply 28, is connected to the tube 23 by sterile docking. HES is passed to the containment zone 19 and the bag is manipulated to expel, as far as is practical, all air from the containment zone 19. The tube 23 is then sealed and the tubes 23, 27 separated. The bag 10 is then manipulated to thoroughly mix the red blood cells and HES.

After mixing, a clip 29 (FIG. 2) is used to close the tube 23 adjacent the port 17, the tube 23 is positioned within the pouch 21, air is expelled from the pouch 21 (by, example, use of a press) and top edges 22 of the sheets 11 are welded together to seal the pouch 21. The bag is then positioned in a freezing frame (a procedure well known in the art, and hence not described here) which is placed in known fashion in liquid nitrogen to freeze the mixture. The clip 29 is helps to prevent blood cells from being drawn from the containment area 19 into the tube 23 during the freezing process. Whilst it is not necessary to evacuate and seal the pouch 21 doing so prevents liquid nitrogen from directly accessing the area of the insert 16 and port 17 so ensuring that nitrogen cannot enter the containment area even if there is a weakness in the juncture of the insert 16 and weld 18.

Once the mixture has been frozen the bag is stored according to the method of PCT/GB/90/0140.

In order to meet the stringent requirements of the method of PCT/GB90/0140 (i.e. controlling an optimum thickness of contents when freezing a standard unit of blood) the containment zone has an area of approximately 0.102 sq. meters, and the welds 15, 18 at the corners of the containment zone 19 are curved. The containment zone 19, apart from the pocket 20, is advantageously rectangular, almost square, in shape, and suitable approximate dimensions are similar to those shown in FIG. 1, namely an overall bag length of 395 mm and width of 325 mm, with lengths between weld 18 and weld 15 at the bottom edge 12, at ends of the pocket 20, being respectively 340 and 300 mm with welds 15 18 4 mm wide, weld 15 being inset 6 mm from edges 14, 13 of sheets 11 and corners having radii of 46 mm. At the corners of the bottom edge 12, external to the containment zone 19, are two reinforced hanging apertures 30.

When the stored blood is required it is thawed according to the method of PCT/GB/90/0140 and the tube 23 connected by a sterile docking device to any regular transfusion bag. The thawing process, which is extremely simple, is the only task not familiar to those used to giving blood transfusions and the blood for transfusion is presented to medical and nursing staff in a bag with which they are familiar.

As the absolute microbiological integrity of the blood is not compromised during donation, storage, thawing, or transfer from the freezing bag 10;

a) the blood can be stored for a time in a normal blood bank after thawing, if it is not required for transfusion immediately, b) an optimal additive solution can be added to prolong the shelf life of the blood, c) a unit of blood can be washed, if this is thought to be required, d) plasma, autologous or homologous, can be added to the red cells in a sterile manner, and e) after the blood has been removed from the freezing bag 10 it is possible to segmentalise the outlet tube 23 to allow numerous cross-matches to be performed with the blood remaining therein.

This design of bag is easy to label in a manner which will prevent transfusion of an incorrect unit, to allow a unit to be traced back to the donor, and otherwise. The label can be attached to one of the sheets 11 in the area forming the pouch 21 as a donation is being transferred to the containment zone 19, minimising the danger of incorrect labelling. A label in this area will not affect heat transfer from the mixture during the freezing process.

Whilst the sheets 11 have been described as single layers it will be realised that each sheet might in fact be multi-layered.

Materials suitable for use with the invention are Kapton F and Teflon, although other suitable materials will be readily apparent to those skilled in the art. Many plastic materials have the required flexibility and resistance to low temperatures. For example metallised plastic material may be used. Depending on the material used, it may be possible to form the bag 10 using a single welding process rather than using two welds 15, 18 as described above.

It will also be realised that the dimensions and thicknesses quoted above are examples only, and may be varied.

Figure 7:
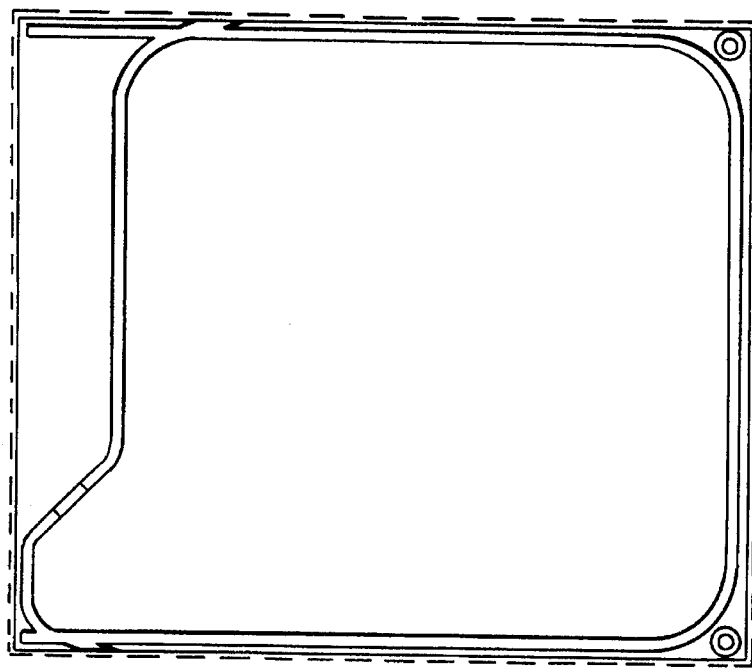
Figure 6:
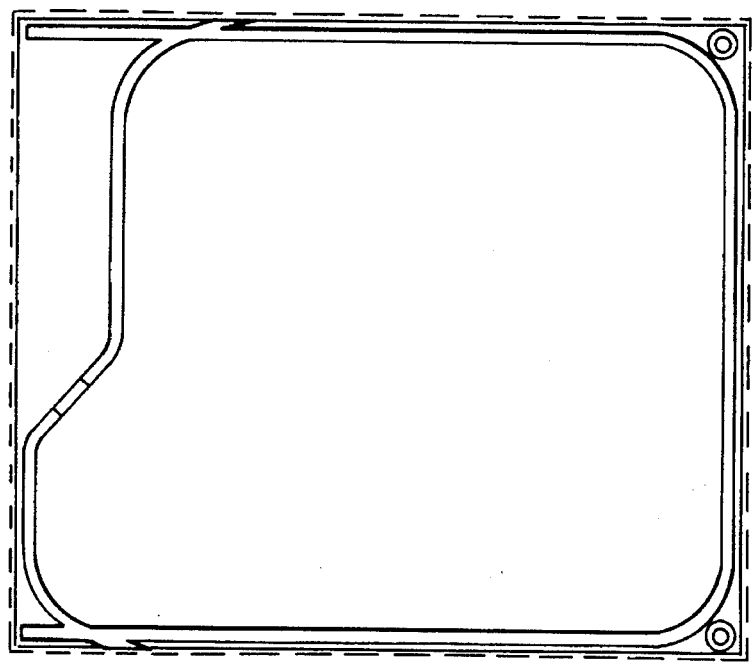

Other embodiments of bag are illustrated in FIGS. 5 to 7, and other embodiments of the above described ideas, within the scope of the invention, will also be readily apparent to those skilled in the art.

What is claimed is:

1. A freezing bag comprising:
   two sheets of a weldable plastic material joined together by a weld defining a containment zone having a bottom edge, two side edges and an access edge said sheets including ends,
   a single access port in the access edge wherein the ends of the sheets of material extend beyond the limits of the containment zone and comprise an open pouch, the pouch being defined by the access edge of the containment zone, extensions of the weld forming the side edges of the containment zone, and ends of the sheets.

2. A freezing bag as claimed in claim 1 wherein the port is situated in a pocket defined in part by at least part of the access edge and which leads into the containment zone.

3. A freezing bag as claimed in claim 2 wherein the pocket is formed by angling of the access edge at other than a right angle to the side edges.

4. A freezing bag as claimed in claim 1 wherein a tube is positioned on the port.

5. A freezing bag as claimed in claim 6 wherein the tube is secured to the port.

6. A freezing bag as claimed in claim 7 wherein the tube is secured to the port by a metal collar.

7. A freezing bag as claimed in claim 1 wherein a tube positioned on the port is preformed to lie within the bounds of the pouch.

8. A freezing bag as claimed in claim 1 wherein the port is formed integrally with an insert which is positioned in the access edge of the bag prior to welding of that edge.

9. A freezing bag as claimed in claim 1 wherein the containment zone and pocket have an area of approximately 0.102 square meters.

10. A freezing bag as claimed in claim 1 wherein the weld, at the corners between the edges, is radiussed.

11. A method of freezing red blood cells comprising the steps of:
    providing a freezing bag, the bag being formed form two sheets of weldable plastic material welded together to form a containment zone having a bottom edge, two side edges and an access edge, at least part of the access edge defining part of a pocket which leads into the containment zone, that part of the access edge having therein an insert having a port to which port is attached a tube, the tube lying within an open pouch formed by extensions of the sheets beyond the extent of the containment zone;
    connecting the tube to a supply of centrifuged and buffy-coat depleted red blood cells;
    transferring the red blood cells to the bag;
    disconnecting the supply of red blood cells;
    sterile docking the tube to a supply of HES;
    transferring the HES to the bag;
    manipulating the bag to expel air therefrom;
    sealing the tube and simultaneously breaking the docking to the HES supply;
    agitating the contents of the bag to thoroughly mix the blood cells and the HES; and
    placing the bag in a freezing frame and freezing the contents by immersing the frame and bag in liquid nitrogen.

12. A method of freezing red blood cells as claimed in claim 11 wherein, before immersing the bag in liquid nitrogen, the pouch is treated to expel air therefrom and its open end sealed with the tube completely contained within the sealed pouch.

13. A method of freezing red blood cells as claimed in claim 11 wherein the tube adjacent the port is clipped during the freezing process.

14. A freezing bag comprising:
    two sheets of bondable plastic material joined together by a bonded peripheral seal, the seal being made to define a containment zone between the sheets, the containment zone having a bottom edge, two side edges and an access edge;
    a pocket leading into the containment zone and formed from part of the access edge;
    a single access port positioned in a part of the access edge forming the pocket;
    a tube secured to the access port; and
    an open pouch formed from extensions of sheets beyond the containment zone and pocket, the pouch being defined by the access edge and extensions of the seal forming the side edges beyond the access edge and the ends of the sheets so as to provide a sealable closure for retaining the tube therein during freezing.

15. A freezing bag as claimed in claim 14 wherein the pocket is formed by angling of the access edge at other than a right angle to the side edges.

16. A freezing bag as claimed in claim 14 wherein the tube is secured to the port by a metal collar.

17. A freezing bag as claimed in claim 14 wherein the tube is preformed to lie within the bounds of the pouch.

18. A freezing bag as claimed in claim 14 wherein the seal at the corners between the edges is radiussed.

19. A freezing bag as claimed in claim 14 wherein the port is formed integrally with an insert which is positioned in the access edge prior to bonding of that edge.

20. A method of freezing red blood cells comprising the steps of:
    providing a freezing bag as claimed in claim 14;
    connecting the tube to a supply of centrifuged and buffy-coat depleted red blood cells and transferring the red blood cells to the bag;
    disconnecting the supply of red blood cells, sterile docking the tube to a supply of hydroxyethyl starch (HES) and transferring the HES to the bag;
    manipulating the bag to expel air therefrom;
    sealing the tube and simultaneously breaking the docking to the HES supply;
    agitating the contents of the bag to thoroughly mix the blood cells and the HES;
    treating the pouch to expel air therefrom and sealing the pouch to completely contain the tube therein; and
    placing the sealed bag in a freezing frame and freezing the contents by immersing the frame in liquid nitrogen.

21. A method of freezing red blood cells as claimed in claim 20, wherein the tube adjacent the port is clipped during the freezing process.

* * * * *